United States Patent
Lu et al.

(10) Patent No.: US 10,175,163 B2
(45) Date of Patent: Jan. 8, 2019

(54) AQUEOUS SAMPLE FLUID MEASUREMENT AND ANALYSIS

(71) Applicant: Hach Company, Loveland, CO (US)

(72) Inventors: Zhao Lu, Fort Collins, CO (US); Brian Harmon, Loveland, CO (US)

(73) Assignee: HACH COMPANY, Loveland, CO (US)

( * ) Notice: Subject to any disclaimer, the term of this patent is extended or adjusted under 35 U.S.C. 154(b) by 0 days.

(21) Appl. No.: 15/281,678

(22) Filed: Sep. 30, 2016

(65) Prior Publication Data

US 2017/0097300 A1    Apr. 6, 2017

Related U.S. Application Data

(60) Provisional application No. 62/239,644, filed on Oct. 9, 2015, provisional application No. 62/236,672, filed on Oct. 2, 2015.

(51) Int. Cl.
| | | |
|---|---|---|
| *G01N 21/27* | (2006.01) | |
| *G01N 33/18* | (2006.01) | |
| *G01N 21/78* | (2006.01) | |

(52) U.S. Cl.
CPC .......... *G01N 21/27* (2013.01); *G01N 21/78* (2013.01); *G01N 33/1853* (2013.01); *G01N 2201/0221* (2013.01); *G01N 2201/12* (2013.01)

(58) Field of Classification Search
CPC ............... G01N 21/27; G01N 33/1853; G01N 2201/12; G01N 21/8483
See application file for complete search history.

(56) References Cited

U.S. PATENT DOCUMENTS

| | | | | |
|---|---|---|---|---|
| 4,102,177 A | * | 7/1978 | Okada ................ | G01N 15/06 250/575 |
| 5,553,616 A | * | 9/1996 | Ham ................ | A61B 5/14558 128/925 |

(Continued)

FOREIGN PATENT DOCUMENTS

| | | |
|---|---|---|
| WO | 2004/063393 | 7/2004 |
| WO | 2009/061729 | 5/2009 |

OTHER PUBLICATIONS

European Patent Office, Communication, Extended European Search Report, dated Jan. 26, 2017, 13 pages.

*Primary Examiner* — Sang Nguyen
(74) *Attorney, Agent, or Firm* — Ference & Associates LLC

(57) ABSTRACT

An embodiment provides a method for determining a concentration of an analyte in a fluid sample, including: introducing a fluid sample into a measurement chamber; operating a measurement device to introduce light of a first wavelength to the fluid sample; measuring, with a detector, absorbance of the light of the first wavelength with respect to the fluid sample; operating the measurement device to introduce light of a second wavelength to the fluid sample; measuring, with the detector, absorbance of the light of the second wavelength with respect to the fluid sample; determining, using a processor of the measurement device, an absorbance ratio of the fluid sample using both the measured absorbance of the light of the first wavelength and the measured absorbance of the light of the second wavelength; and providing, via an output device, a determined concentration value for the fluid sample that correlates to the absorbance ratio. Other aspects are described and claimed.

16 Claims, 4 Drawing Sheets

(56) References Cited

U.S. PATENT DOCUMENTS

| | | | | |
|---|---|---|---|---|
| 7,473,229 B2* | 1/2009 | Webber | ............... | A61B 5/0836 |
| | | | | 422/84 |
| 2003/0025909 A1* | 2/2003 | Hallstadius | ............. | A23L 3/003 |
| | | | | 356/436 |
| 2005/0221499 A1 | 10/2005 | Mitsumoto | | |
| 2006/0238764 A1 | 10/2006 | Hafeman et al. | | |
| 2008/0087819 A1* | 4/2008 | Kalveram | .......... | G01N 21/8483 |
| | | | | 250/307 |
| 2008/0144005 A1* | 6/2008 | Guiney | ............. | G01N 21/3151 |
| | | | | 356/39 |
| 2012/0021527 A1 | 1/2012 | Salzer et al. | | |
| 2013/0052742 A1 | 2/2013 | Davis et al. | | |
| 2013/0283889 A1* | 10/2013 | Yamada | ............. | G01N 33/0031 |
| | | | | 73/31.06 |
| 2013/0330245 A1 | 12/2013 | Duncan et al. | | |
| 2014/0152992 A1* | 6/2014 | Kendall | ................... | G01J 3/10 |
| | | | | 356/445 |
| 2015/0037898 A1* | 2/2015 | Baldus | ............... | G01N 21/8483 |
| | | | | 436/93 |

* cited by examiner

AQUEOUS SAMPLE FLUID MEASUREMENT AND ANALYSIS

BACKGROUND

Analysis of fluids is useful in many applications. For example, measurement of water's hardness may be of importance, as hard water may be undesirable in certain contexts. Accordingly, colorimetric methods for analyzing water hardness have been developed. Colorimetery uses a color change in the sample fluid as representative of an amount of a substance of interest, e.g., a component in an aqueous sample fluid that reacts with a reagent to form a colored product. The colored product may be measured by light absorbance.

It has been observed that in certain cases colorimetric measurements of water vary away from an expected linear response. That is, the amount of color change does not linearly correspond to the amount of substance of interest. Many factors may contribute to this. For example, a sample's volume, the indicator (color) amount added to a sample, the reagent solubility in the sample, etc., may affect the measured color such that it varies away from a linear response. This variation away from linearity often takes place at the ends of the measurable range (e.g., high and low ends of the measurable range). The variation away from linearity causes inaccurate measurement.

BRIEF SUMMARY

In summary, one embodiment provides a method for determining a concentration of an analyte in a fluid sample, comprising: introducing a fluid sample into a measurement chamber; operating a measurement device to introduce light of a first wavelength to the fluid sample; measuring, with a detector, absorbance of the light of the first wavelength with respect to the fluid sample; operating the measurement device to introduce light of a second wavelength to the fluid sample; measuring, with the detector, absorbance of the light of the second wavelength with respect to the fluid sample; determining, using a processor of the measurement device, an absorbance ratio of the fluid sample using both the measured absorbance of the light of the first wavelength and the measured absorbance of the light of the second wavelength; and providing, via an output device, a determined concentration value for the fluid sample that correlates to the absorbance value.

An embodiment provides an apparatus, comprising: a measurement chamber; a light source; a light detector; an output device; and a memory having instructions that execute by a processor to: operate the light source to introduce light of a first wavelength to a fluid sample in the measurement chamber; measure, with the light detector, absorbance of the light of the first wavelength with respect to the fluid sample; operate the light source to introduce light of a second wavelength to the fluid sample; measure, with the light detector, absorbance of the light of the second wavelength with respect to the fluid sample; determine an absorbance ratio of the fluid sample using both the measured absorbance of the light of the first wavelength and the measured absorbance of the light of the second wavelength; and provide, via the output device, a determined concentration value for the fluid sample that correlates to the absorbance ratio.

An embodiment provides a program product, comprising: a storage device that stores code that is executable by a processor, comprising: code that operates a light source to introduce light of a first wavelength to a fluid sample in a measurement chamber; code that measures, with a light detector, absorbance of the light of the first wavelength with respect to the fluid sample; code that operates the light source to introduce light of a second wavelength to the fluid sample; code that measures, with the light detector, absorbance of the light of the second wavelength with respect to the fluid sample; code that determines an absorbance ratio of the fluid sample using both the measured absorbance of the light of the first wavelength and the measured absorbance of the light of the second wavelength; and code that provides, via an output device, a determined concentration value for the fluid sample that correlates to the absorbance ratio.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
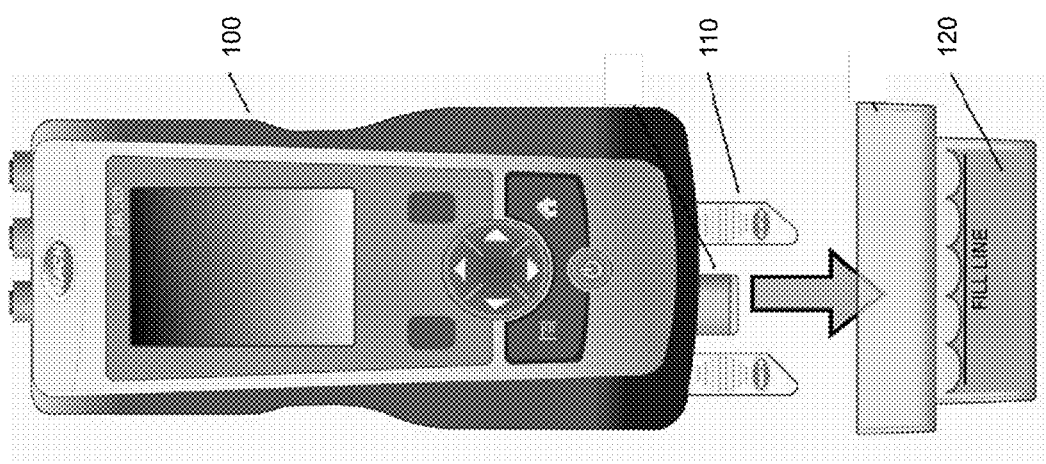
FIG. 1 illustrates an example measurement system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

While the various embodiments may be implemented in a variety of fluid measurement/analysis instruments, for the purpose of concise description, an example embodiment is described with reference to a chip-based chemistry product and associated methods. It will be appreciated by those having ordinary skill in the art that the various techniques described in connection with the example embodiments may be applied to other devices.

It can be advantageous to conduct chemical analyses in the field, for example optical or colorimetery-based testing for determining characteristics of water. Outside of a laboratory setting, a hand-held or similar mobile instrument affording accurate and precise chemical analysis is desirable, as may be used in compliance monitoring in connection with water treatment processes.

In the non-limiting example of water hardness measurements, the hardness of a water sample may be determined via a color based reaction with an indicator such as a dye component because the reaction produces a colored product in known proportion that in turn can be measured via a color sensitive sensor or detector, for example, indicating a degree of light absorption of the colored product relative to a baseline, reference solution. Water hardness is attributed to dissolved minerals contained in the water. The minerals include polyvalent cations such as calcium, magnesium, iron, manganese, and zinc. The concentration of calcium and magnesium in natural waters generally exceeds other polyvalent cations. Therefore, hardness is generally considered to be the concentration of calcium and magnesium in water.

Water hardness is commonly measured by titration, e.g., with an EDTA solution. Titration involves adding a solution to a water sample until the sample changes color. More than one titration may be done, e.g., one can measure calcium hardness separately from magnesium hardness by adjusting the pH and using different indicators.

Referring to FIG. 1, embodiments provide devices and associated methods for chip based chemical analyses, such as measurement of water hardness. In such a system, a chip or cuvette 110 contains a fluid channel (internally, not shown in FIG. 1) that may include necessary chemicals in or along the fluid channel, e.g., a component added to shift the water sample's color for measuring water hardness.

The cuvette 110 is dipped into the fluid 120 in order to introduce the fluid into the cuvette 110. The fluid 120 (e.g., water for hardness testing) is moved along the fluid channel from an inlet and is mixed with chemical(s) as it is drawn through the fluid channel, in one or both directions, by operation of a pneumatic pump or like arrangement contained in a hand held measurement instrument 100. The hand held measurement instrument 100 moves the sample fluid in the fluid channel in a timed way, allowing for timed mixing and sequential addition of the chemicals, along with optical measurements.

As the measurement instrument 100 draws the fluid sample, e.g., about 30 µl, into the fluid channel of the cuvette 110 from a sample cup 120, the measurement instrument 100 moves the fluid sample via pneumatic pressure in one or both directions within the fluid channel. The movement of the sample fluid contacts the fluid with the reagent chemical(s) contained in the fluid channel. This permits addition of reagents to the fluid in a precise fashion and timing to achieve various aims relevant to chemical analyses.

An embodiment provides for first obtaining a treated fluid sample measurement (e.g., of colored fluid) in an optical channel (optical portion of the fluid channel) using optics and a detector such that light of a given wavelength is transmitted into the fluid sample and absorbance (or transmission) may be measured. The color of the sample fluid affects the absorbance (or transmission) of the light, changing the detected light and thus the read out of the measurement instrument 100.

Once an optical measurement is obtained, the fluid sample may be progressed further along the fluid channel, past the optical chamber, and contacted with additional chemicals. Additionally, an embodiment may transmit light of more than one wavelength into the fluid sample, either at the same time or in separate measurements.

An embodiment provides for increased linearity of measurements over a broader range of water hardness by employing a ratio technique. For example, the linear dynamic range may be increased and variation reduced for hardness detection when using colorimetery by using two or more wavelengths of light to measure the hardness of the fluid sample and reporting a hardness value based on the ratio of these measurements.

Figure 2:
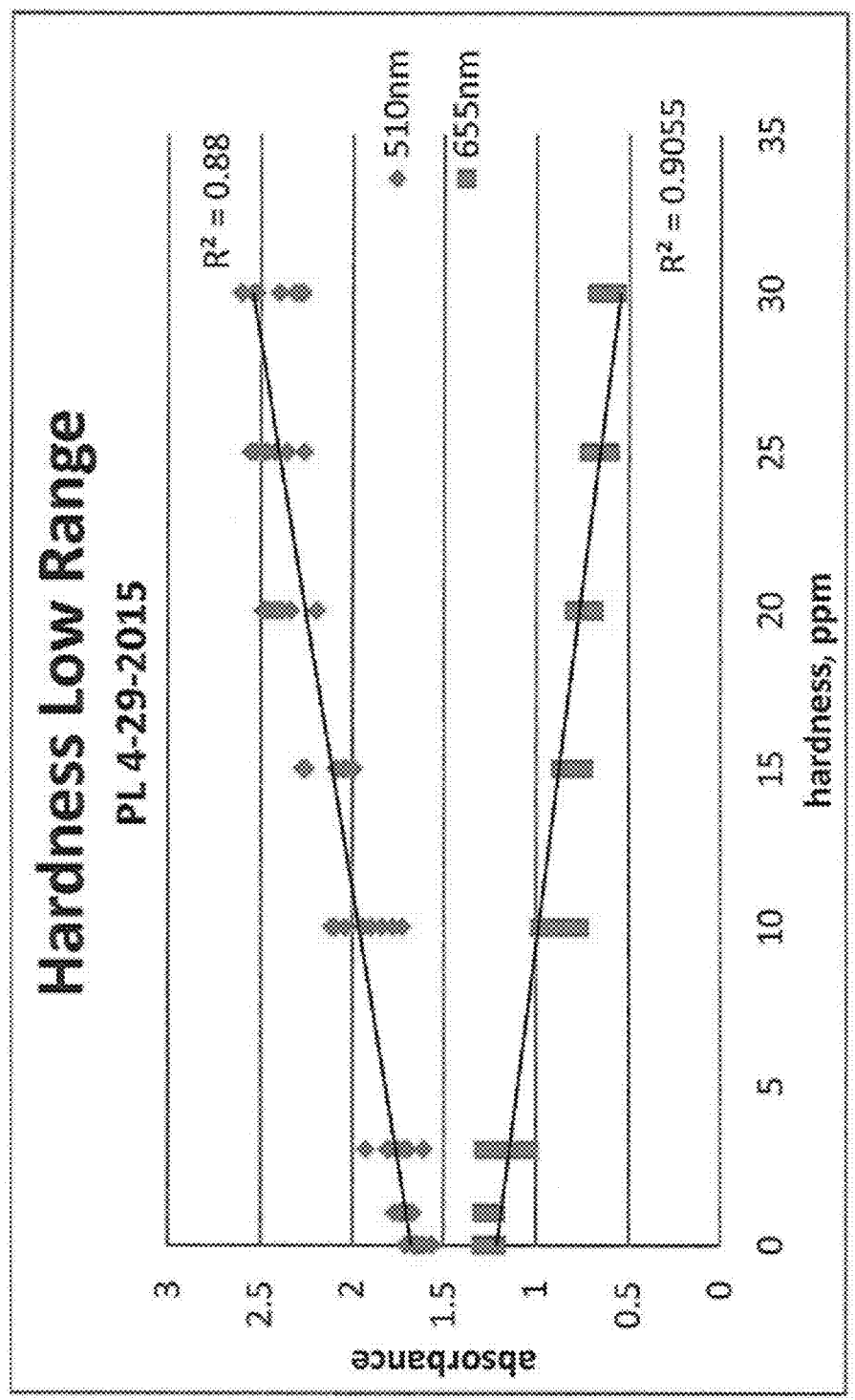
FIG. 2 illustrates example absorbance measurements at 510 nm and at 655 nm individually.

By way of specific example, and referring to FIG. 2, for low range hardness detection in the parts per million (ppm) range (e.g., about 0 ppm to 20 ppm), the absorbance measurements are not linear (refer to $R^2$ values) for either 510 nm light or 655 nm light individually.

Figure 3:
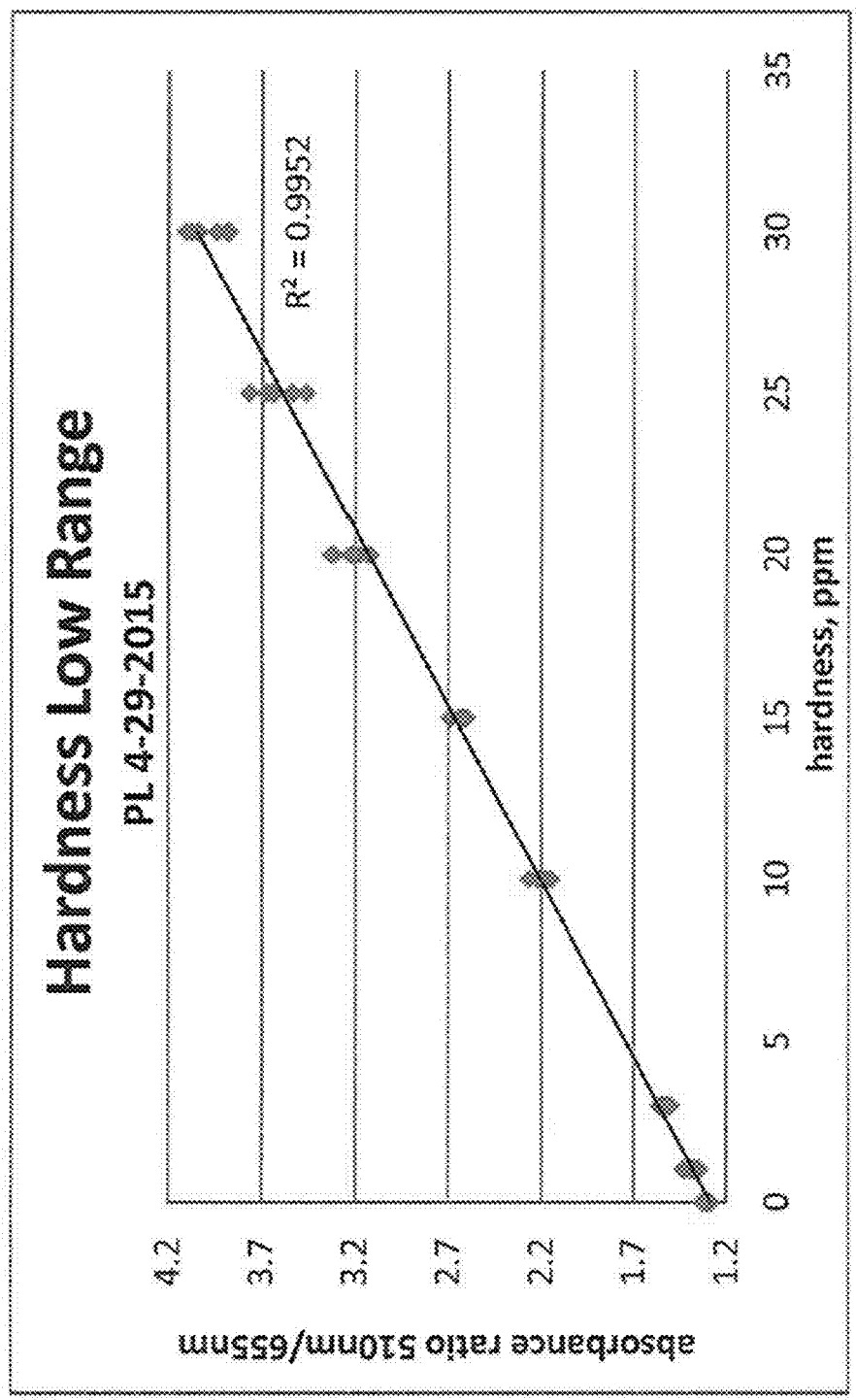
FIG. 3 illustrates example ratio absorbance measurements for two wavelengths (510 nm and 655 nm).

However, and referring to FIG. 3, the absorbance measurements may be reported as a ratio, e.g., 510 nm/655 nm, whereby the linearity of the reported value is increased (again refer to the $R^2$ value). Thus, an embodiment may maintain the linearity of the absorbance measurements through a greater range (in the illustrated example in a low end of the range).

In the measurement examples of FIG. 2 and FIG. 3, the measurements reported are water hardness measurements. Indicators that may be used include but are not limited to Mordant Blue 13 (for low range hardness) and calmagite (for high range hardness). Both Mordant Blue 13 and calmagite indicators are in the same family of diazo compound. As illustrated, absorbance at 510 nm and 655 nm individually was not linear. Linearity was found applying the ratio method and variations in absorbance measurements were also reduced using the ratio method. The measurements may be taken using a HACH SL1000 PORTABLE PARALLEL ANALYZER measurement instrument, as described herein.

In table 1 a comparison of the detection limit using 510 nm absorbance, 655 nm absorbance, and the ratio of 510 nm/655 nm absorbance is provided. As may be appreciated, the detectable limit is reduced when the ratio technique is employed.

|  | MDL, ppm |
| --- | --- |
| Using 510 nm absorbance detection | 3.18 |
| Using 655 nm absorbance detection | 3.53 |
| Using ratio absorbance detection | 0.86 |

Figure 4:
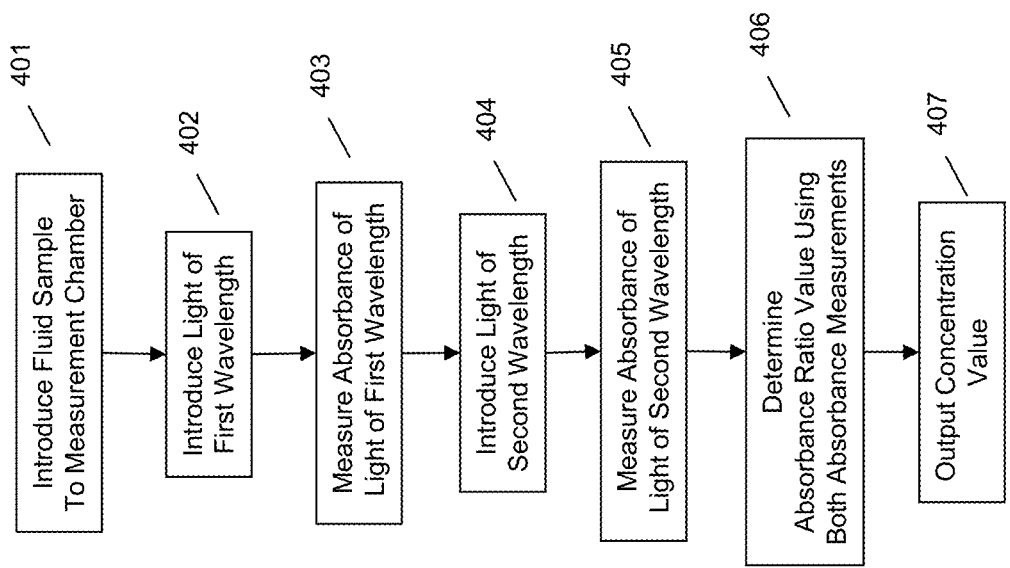
FIG. 4 illustrates an example method of water hardness measurement.

Turning to FIG. 4, an embodiment includes a method where a fluid sample is introduced into a measurement chamber at 401. The fluid sample may be a water sample having one or more reagents added thereto in order to produce a colored product in accordance with a water hardness measurement. A measurement device is then operated to introduce light of a first wavelength to the fluid sample at 402, where a detector of the measurement device detects absorbance of the light of the first wavelength with respect to the fluid sample at 403. Thereafter or at substantially the same time, the measurement device is operated to introduce light of a second wavelength to the fluid sample at 404, where a detector of the measurement device detects absorbance of the light of the second wavelength with respect to the fluid sample at 405.

Having the first and second absorbance measurements, and optionally repeating this process with other wavelengths of light, an embodiment may determine at 406, e.g., using a processor of the measurement device, a calculated value of the fluid sample using both the measured absorbance of the light of the first wavelength and the measured absorbance of the light of the second wavelength. As described herein, this may include taking the ratio of absorbance values obtained for the individual wavelengths. Having an absorbance ratio, an embodiment may then provide, e.g., via an output device such as a display screen, a determined concentration value for the fluid sample at 407. The determined concentration value may be output as a converted value, e.g., ppm or the like, depending on the measurement of the fluid sample being conducted.

In an embodiment, the determining step at 406 may include determining a ratio of the measured absorbance of the light of the first wavelength and the measured absorbance of the light of the second wavelength.

In an embodiment, the first wavelength is about 510 nm and the second wavelength is about 655 nm.

In an embodiment, the fluid sample is water and the determined concentration value is reported in ppm.

As described herein, applying a ratio technique to convert individual absorbance values into a ratio of absorbance values results in extending the range at which linear absorbance measurements may be obtained. Thus, in an embodiment, the determined concentration value is in a range of about 3 to about 25 ppm. Also, in an embodiment, the determined concentration value is in a range of about 20 to about 100 ppm.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for determining a concentration of an analyte in a fluid sample, comprising:
   introducing a fluid sample into a measurement chamber, wherein the fluid sample is a water;
   operating a measurement device to introduce light of a first wavelength to the fluid sample;
   measuring, with a detector, absorbance of the light of the first wavelength with respect to the fluid sample;
   operating the measurement device to introduce light of a second wavelength to the fluid sample;
   measuring, with the detector, absorbance of the light of the second wavelength with respect to the fluid sample;
   determining, using a processor of the measurement device, an absorbance ratio of the fluid sample using both the measured absorbance of the light of the first wavelength and the measured absorbance of the light of the second wavelength; and
   providing, via an output device, a determined concentration value for the fluid sample that correlates to the absorbance ratio, wherein the determined concentration value is in a range of about 3 to about 25 ppm.

2. The method of claim 1, wherein the first wavelength is about 510 nm.

3. The method of claim 2, wherein the second wavelength is about 655 nm.

4. The method of claim 1, wherein the determined concentration value is reported in parts per million (ppm).

5. The method of claim 4, wherein the determined concentration value is in a range of about 20 to about 100 ppm.

6. The method of claim 1, wherein the determined concentration value is a water hardness value.

7. An apparatus, comprising: a measurement chamber; a light source; a light detector; an output device; and a memory having instructions that execute by a processor to:

operate the light source to introduce light of a first wavelength to a fluid sample in the measurement chamber, wherein the fluid sample is a water;

measure, with the light detector, absorbance of the light of the first wavelength with respect to the fluid sample;

operate the light source to introduce light of a second wavelength to the fluid sample;

measure, with the light detector, absorbance of the light of the second wavelength with respect to the fluid sample;

determine an absorbance ratio of the fluid sample using both the measured absorbance of the light of the first wavelength and the measured absorbance of the light of the second wavelength; and provide, via the output device, a determined concentration value for the fluid sample that correlates to the absorbance ratio, wherein the determined concentration value is in a ramie of about 3 to about 25 ppm.

8. The apparatus of claim 7, wherein the first wavelength is about 510 nm.

9. The apparatus of claim 8, wherein the second wavelength is about 655 nm.

10. The apparatus of claim 7, wherein the light source comprises more than one light source.

11. The method of claim 7, wherein the determined concentration value is reported in parts per million (ppm).

12. The method of claim 11, wherein the determined concentration value is in a range of about 20 to about 100 ppm.

13. The method of claim 7, wherein the determined concentration value is a water hardness value.

14. A program product, comprising:
a non-transitory storage device that stores code that is executable by a processor, comprising:
code that operates a light source to introduce light of a first wavelength to a fluid sample in a measurement chamber, wherein the fluid sample is a water;
code that measures, with a light detector, absorbance of the light of the first wavelength with respect to the fluid sample;
code that operates the light source to introduce light of a second wavelength to the fluid sample;
code that measures, with the light detector, absorbance of the light of the second wavelength with respect to the fluid sample;
code that determines an absorbance ratio of the fluid sample using both the measured absorbance of the light of the first wavelength and the measured absorbance of the light of the second wavelength; and
code that provides, via an output device, a determined concentration value for the fluid sample that correlates to the absorbance ratio, wherein the determined concentration value is in a ramie of about 3 to about 25 ppm.

15. The program product of claim 14, wherein the first wavelength is about 510 nm.

16. The program product of claim 15, wherein the second wavelength is about 655 nm.

* * * * *